(12) United States Patent
Jansen et al.

(10) Patent No.: US 7,342,123 B2
(45) Date of Patent: Mar. 11, 2008

(54) HIGH TEMPERATURE-STABILE SILICON BORON CARBIDE NITRIDE CERAMICS COMPRISED OF SILYLALKYL BORAZINES, METHOD FOR THE PRODUCTION THEREOF, AND THEIR USE

(75) Inventors: Martin Jansen, Leonberg (DE); Thomas Jaschke, Stuttgart (DE)

(73) Assignee: Max-Planck-Gesellschaft zur Forderung der Wissenschaften E.V., Munich (DE)

( * ) Notice: Subject to any disclaimer, the term of this patent is extended or adjusted under 35 U.S.C. 154(b) by 0 days.

(21) Appl. No.: 11/555,934

(22) Filed: Nov. 2, 2006

(65) Prior Publication Data

US 2007/0063396 A1 Mar. 22, 2007

Related U.S. Application Data

(62) Division of application No. 10/380,553, filed on Mar. 12, 2000, now Pat. No. 7,148,368.

(30) Foreign Application Priority Data

Sep. 12, 2000 (DE) .................. 100 45 050
Feb. 20, 2001 (DE) .................. 101 08 069

(51) Int. Cl.
*C07F 7/02* (2006.01)
(52) U.S. Cl. .................................... 556/402

(58) Field of Classification Search ............... None
See application file for complete search history.

(56) References Cited

U.S. PATENT DOCUMENTS 6,093,840 A 7/2000 Jansen et al.

FOREIGN PATENT DOCUMENTS

| DE | 34 44 306 A | 6/1985 |
| WO | WO 98 45302 | 10/1998 |
| WO | WO 98 45303 | 10/1998 |
| WO | WO 01 53304 | 7/2001 |

OTHER PUBLICATIONS

Kiesgen, Jutta et al., "A further contribution to the stabilization of iminoboranes RB.tplbond.nr," Chem. Ber. vol. 126, No. 7, 1993, pp. 1559-1563.

McMullen, (Rearrangement in Borane Adducts of Trimethylsilylmethylenedimethylsulfurane, Inorganic Chemistry, vol. 9, No. 10 1970, 2291-2295).

*Primary Examiner*—Samuel A Barts
(74) *Attorney, Agent, or Firm*—Sutherland Asbill & Brennan LLP

(57) ABSTRACT

The present invention concerns a process for producing silylalkylboranes containing the structural feature Si—C—B, new molecular silylalkylboranes, new molecular silylalkylborazines, new oligoborocarbosilazanes and polyborocarbosilazanes, a process for their production and their use as well as silicon boron carbide nitride ceramics and a process for their production.

3 Claims, No Drawings

HIGH TEMPERATURE-STABILE SILICON BORON CARBIDE NITRIDE CERAMICS COMPRISED OF SILYLALKYL BORAZINES, METHOD FOR THE PRODUCTION THEREOF, AND THEIR USE

CROSS REFERENCE TO RELATED APPLICATIONS

This application is a divisional of U.S. application Ser. No. 10/380,553 filed on Mar. 12, 2003, allowed, which claims priority to PCT Patent Application No. WO02/22625 filed Sep. 12, 2001 and German Patent Applications No. 100 45 050.4 filed Sep. 12, 2000 and 101 08 069.7 filed Feb. 20, 2001.

The present invention concerns a process for producing silylalkylboranes containing the structural feature Si—C—B, new molecular silylalkylboranes, new molecular silylalkylborazines, new oligoborocarbosilazanes and polyborocarbosilazanes, a process for their production and their use, as well as high-carbon silicon boron carbide nitride ceramics and a process for their production.

The production of non-oxidic multinary ceramics by cross-linking molecular precursors is of supreme importance. Ceramic materials of high purity which have a homogeneous distribution of elements at the atomic level can at present only be produced by this method. Such materials cannot be prepared by means of conventional synthetic pathways such as solid-state reactions.

Nitride and carbide-nitride ceramics containing boron and silicon have become particularly important. They have a high thermostability and oxidation resistance and exhibit a pronounced crystallization inhibition. The thermal stability of ceramics in this quarternary system can be increased by additionally incorporating carbon into the ceramic network. Such materials are excellently suitable for use at high temperatures under atmospheric conditions and can be used as a bulk material, as ceramic fibres in composite materials, the form of coatings or they can be used for microstructural processes.

The synthesis of the single component precursor trichlorosilylaminodichloroborane (TADB, $Cl_3Si$—NH—$BCl_2$) is described in the patent DE 4 107 108 A1 which results in a ceramic of the approximate composition $SiBN_3$ after cross-linking with methylamine and subsequent pyrolysis in a stream of inert gas. The carbon which it contains is derived from the methyl group of the cross-linking reagent methylamine, A disadvantage of this process is the limited ability to vary the carbon content which can only be adjusted by using a longer alkyl group in the cross-linking reagent. However, this alkyl group is lost during the pyrolysis in the form of volatile hydrocarbons or it leads to undesired graphite deposits in the ceramic.

The patent WO 98/45302 describes the production of high-carbon ceramics in the Si/B/N/C system from a single-component precursor which has a branched carbon bridge between the elements boron and silicon. This allows the synthesis of ceramics which have a higher carbon content. A disadvantage of this process is that the single-component precursor has an alkyl group at the carbon bridge which can be lost during pyrolysis in the form of volatile hydrocarbons.

Hence an object of the present invention was to provide a simple process which yields the single-component precursor in high yields and does not have the disadvantages of the prior art. In particular the process should also allow the preparation of precursor compounds without branched alkyl groups which can then be further processed to amorphous or partially crystalline high carbon ceramics.

Another object was to provide amorphous Si/B/N/C ceramics, having an improved high temperature and oxidation stability.

This object is achieved according to the invention by a process for producing a compound of formula (I)

$(R)_3Si$—$C(R^1)(R^2)$—$B(R)_2$      (I)

in which R in each case independently denotes a hydrocarbon with 1 to 20 C atoms, hydrogen, halogen, NR'R" or OR' where R' and R" independently of one another, denote hydrogen or a hydrocarbon with 1 to 20 C atoms and $R^1$ and $R^2$ denote independently of one another a hydrocarbon with 1 to 20 C atoms, hydrogen, halogen, NR'R" or OR' where R' and R" independently of one another, denote hydrogen or a hydrocarbon with 1 to 20 C atoms.

In the process according to the invention a silane of the general formula (II)

$(R)_3Si$—$C(R^1)(R^2)$—X      (II)

in which X denotes halogen, is reacted with a metal M e.g. an alkali metal such as Na, K and in particular Li, an alkaline earth metal in particular Mg or a transition metal such as Cu, Zn, Cd, Hg. The reaction takes place at temperatures in which essentially no polymerization occurs and in particular below 50° C. and particularly preferably between 0° C. and 15° C. in an aprotic organic solvent and yields a silane of the general formula (III)

$(R)_3Si$—$C(R^1)(R^2)$-$M(X)_w$      (III)

in which w=0 if M is a monovalent metal and
w is an integer $\geq 1$ corresponding to the valence state of M minus 1 if M is a multivalent metal.

As used in this application the residues R, $R^1$, $R^2$, R' and R" can each independently denote a hydrocarbon residue with 1 to 20 C atoms, preferably with 1 to 10 C atoms. A hydrocarbon residue is a residue which is composed of the elements carbon and hydrogen. According to the invention the hydrocarbon residue can be branched or unbranched, saturated or unsaturated. The hydrocarbon residue can also contain aromatic groups which can in turn be substituted with hydrocarbon residues. Examples of preferred hydrocarbon residues are e.g. unbranched saturated hydrocarbon residues such as $C_1$ to $C_{20}$ alkyl, in particular methyl, ethyl, n-propyl, n-butyl, n-pentyl, n-hexyl, n-heptyl, n-octyl, n-nonyl and n-decyl. However, the residues R can also be branched saturated hydrocarbon residues, in particular branched $C_1$ to $C_{20}$ alkyls such as i-propyl, i-butyl, t-butyl and other branched alkyl residues. In another preferred embodiment the residue R contains one or more olefinic unsaturated groups. Examples of such residues are vinyl, allyl, butenyl, pentenyl, hexenyl, heptenyl, octenyl, nonenyl, decenyl, butadienyl, pentadienyl, hexadienyl, heptadienyl, octadienyl, nonadienyl and decadienyl. The residue R can also contain an alkine group i.e. a C≡C bond. In a further preferred embodiment at least one residue R and preferably all residues R contain an aromatic group in particular an aromatic residue with 5 or 6 C atoms such as a phenyl group or a phenyl group substituted with a hydrocarbon such as methylphenyl, dimethylphenyl, trimethylphenyl, ethylphenyl or propylphenyl. The aromatic residue including the substituents preferably contains 5 to 20 and in particular up to 10 C atoms. In this case the hydrocarbon residues R, $R^1$, $R^2$, R', R" can each differ from one another.

At least one residue R, $R^1$, $R^2$, R' or/and R" and in particular all residues R, $R^1$, $R^2$, R' and/or R" particularly preferably contain a $C_1$ to $C_{20}$ alkyl group in particular a $C_1$-$C_6$ alkyl group, a phenyl group, a vinyl group or an allyl group or a hydrocarbon residue with 1 to 3 C atoms in particular methyl, ethyl or propyl and most preferably methyl.

The residue Hal represents a halogen atom and in particular denotes Cl, Br or I and it is preferred that at least one residue denotes Hal and preferably all Hal residues denote Cl.

As described above the compound (III) can, on the one hand, be produced directly from a compound of formula (II) and a metal when a metal of sufficient reactivity is used e.g. Li, Na, K, Mg, Cu, Zn, Cd, Hg. On the other hand, a compound (III) in which M is a metal that is not sufficiently reactive for an efficient direct alkylation e.g. Sn can also be produced in two steps. In the first step a compound (III) containing a directly reactive metal is produced which is then transmetallated in a second step with the not directly reactive metal. The metal can for example be used in the form of metal chips or preferably as a powder.

Subsequently the compound of the general formula (III) is reacted at temperatures below 50° C. and preferably at temperatures between −50° C. and 0° C. with a borane of the general formula

in which R is as defined above and Y represents halogen, NR'R" or OR' where R' and R" independently of one another denote hydrogen or a hydrocarbon with 1 to 20 C atoms.

It is also possible to firstly transfer the silylalkyl residue of formula (III) onto another metal and then to carry out the reaction with the borane.

In a preferred embodiment of the process a chloromethyl silane compound of formula

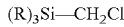

in which R independently of one another can have the meanings stated for the general process, is metallated in a Grignard reaction with magnesium powder and subsequently reacted with the halogen-borane.

The metallation of chloromethyl-alkylchlorosilanes of the general formula $(R_n)(Cl_{3-n})Si(CH_2Cl)$ in which n=0; 1; 2; 3; R=$C_1$-$C_6$ alkyl, vinyl, phenyl, hydrogen, halogen, alkylamino groups N(R')(R"), alkyloxy groups OR' where R', R" can independently of one another be $C_1$-$C_6$ alkyl, vinyl, phenyl, hydrogen or halogen, can for example take place in diethyl ether or tetrahydrofuran.

The silane of the general formula (III) is preferably reacted with at least one alkyloxychloroborane YB($R^3$)($R^{3'}$) in which Y denotes Cl and $R^3$ and $R^{3'}$ independently of one another denote a $C_1$-$C_{20}$ alkoxy or phenyloxy residue.

The halogen boranes YB($R^3$)($R^{3'}$) used in the process according to the invention are particularly preferably alkoxychloroboranes in which Y=Cl, Br and $R^3$, $R^{3'}$ independently of one another denote $C_1$-$C_6$ alkoxy or phenyloxy residues.

Hence another subject matter of the present invention is the reaction of a compound of the general formula (V)

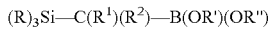

with an element halogenide or an organic acid halogenide.

This results in the formation of a compound of the general formula (IV)

In this formula R, $R^1$ and $R^2$ each independently of one another represent hydrogen, halogen, a hydrocarbon residue with 1 to 20 C atoms, a residue N(R')(R") or a residue OR' in which R" and R' independently of one another denote hydrogen or a hydrocarbon residue with 1 to 20 C atoms and X denotes halogen.

$R^1$ and $R^2$ each preferably denote, independently of one another, either hydrogen or halogen.

In a preferred embodiment of the process according to the invention the intermediate products $(R)_3Si—C(R^1)(R^2)—B(OR')(OR")$ are reacted without prior separation from the reaction mixture with element chlorides or organic acid halogenides and in particular with boron trihalogenides to form

which considerably reduces the work required for the preparation.

In a preferred embodiment the Grignard reaction is carried out using the dilution principle at temperatures below 50° C. in an aprotic organic solvent which can for example be an acyclic or cyclic ether or a $C_5$-$C_8$ alkane.

In order to isolate the pure substances, the solvent is removed by distillation and the product is either fractionally distilled at reduced pressure or purified by recrystallization. Other purification methods can also be used such as e.g. high-performance liquid chromatography (HPLC).

The process according to the invention can also be used to prepare silylalkylboranes of formula (I) that cannot be produced by the process of WO98/45302.

Hence the invention also concerns silylalkylboranes of formula (I)

in which R each independently of one another denotes hydrogen, halogen, a hydrocarbon residue with 1 to 20 C atoms, N(R')(R") or OR' in which R' and R" each independently represent hydrogen or a hydrocarbon residue with 1 to 20 C atoms, and $R^1$ and $R^2$ each independently denote hydrogen, halogen, N(R')(R") or OR', in which R' and R" each independently represent hydrogen or a hydrocarbon residue with 1 to 20 C atoms.

R is preferably in each case independently $C_1$-$C_6$ alkyl, vinyl, phenyl, hydrogen, halogen, organylamino groups N(R')(R"), organyloxy groups OR', where R' R" independently of one another denote $C_1$-$C_6$ alkyl, vinyl, phenyl or hydrogen and $R^1$, $R^2$ are, independently of one another, hydrogen or one of its isotopes or halogen.

The silylalkylborane of formula (I) is preferably one in which at least one of the residues R represents methyl or/and Cl. It is also preferred that $R^1$ and $R^2$ are each hydrogen.

R is particularly preferably in each case independently Cl and/or $CH_3$ and $R^1$ and $R^2$=H.

Particularly preferred embodiments of the inventive silylalkylboranes of formula (I) are compounds in which a halogen and two hydrocarbon residues or two halogens and one hydrocarbon residue are bound to the Si. Such compounds contain one or two hydrocarbon residues on the Si atom which can be used to further increase the carbon content of a ceramic produced from such compounds. In addition such compounds have a reduced content of halogen atoms that react to form oligomers or polymers. As a result it is possible to produce oligomers or polymers having a reduced degree of cross-linking and in particular polymers that have an essentially linear structure. Furthermore compounds of formula (I) are preferred in which two halogen atoms or one halogen atom and one hydrocarbon residue are bound to the boron atom.

Single component precursors of this type in which boron and silicon are linked by a bridge $C(R^1)(R^2)$ can be used to produce polymers in which carbon is a fixed constituent of the polymer independent of the degree of cross-linking. This facilitates the incorporation of carbon into the ceramic network and substantially reduces the cleavage of volatile carbon-containing compounds during the pyrolysis. The C content in the ceramic can be varied within wide limits by the selection of a suitable cross-linking reagent and as a result the spectrum of properties of the ceramics can be specifically adapted to the requirements. Ceramics produced in this manner have excellent high temperature and oxidation stabilities.

The silanes used as the starting products are commercially available like the boron trihalogenides. The borane that is used can be prepared according to J. Chem. Soc. (1957) 501-505, from commercially available boranes.

The invention also concerns silylalkylborazines of formula (X):

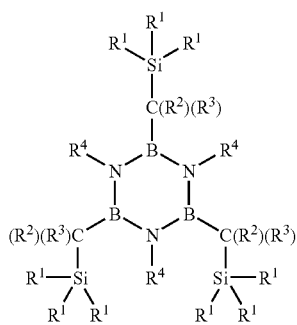

(X)

in which $R^1$ each independently of one another denotes hydrogen, halogen, a hydrocarbon residue with 1 to 20 C atoms, N(R')(R") or OR', in which R' and R" each independently represent hydrogen or a hydrocarbon residue with 1 to 20 C atoms and $R^2$ and $R^3$ each independently denote hydrogen, halogen, N(R')(R") or OR' in which R' and R" each independently represent hydrogen or a hydrocarbon residue with 1 to 20 C atoms and $R^4$ each independently represents $R^1$, $Sn(R^*)_3$ or $Si(R^*)_3$ in which R* each independently denotes $R^2$ or a hydrocarbon residue with 1 to 20 C atoms.

The preferred and particularly preferred residues in the said silylalkylborazines correspond to the residues stated as being preferred for silylalkylboranes.

The silylalkylborazines according to the invention are particularly suitable as precursor compounds and, after polymerization and pyrolysis of the polymers, lead to new amorphous Si/B/N/C ceramics having improved high temperature and oxidation stabilities which were previously unattainable in this system. These new ceramics exhibit almost no loss in mass up to at least 2000° C. or/and are oxidatively stable up to at least 1400° C. in pure oxygen.

The silylalkylboranes according to the invention can be reacted with amines of the type $N(R^4)_3$ or with the corresponding ammonium salts $HN(R^4)_3{}^+A^-$ to form the described silylalkylborazines, in which $R^4$ in each case independently has the above-mentioned meanings. $A^-$ represents any anion and is in particular a halogenide such as $F^-$, $Cl^-$, $Br^-$ or $I^-$, a $SO_4{}^{2-}$ group, an $NO_3{}^-$ group or a nitrite, chlorate, perchlorate, carbamate, tartrate, phosphate, pentaborate, chromate, citrate, hydrogencitrate, carbonate, hydrogencarbonate, triflate, acetate or benzoate group. $A^-$ is preferably a halogenide and particularly preferably a chloride.

The reaction of the silylalkylboranes with the amines or ammonium salts preferably takes place with or without solvent at temperatures between −100° C. and 200° C., more preferably at temperatures between 20° C. and 50° C.

nAnother process for producing silylalkylborazines starts with borazines of the type

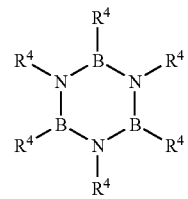

in which $R^4$ in each case independently of one another represents hydrogen, halogen, a hydrocarbon residue with 1 to 20 C atoms, N(R')(R") or OR', in which R' and R" each independently represent hydrogen or a hydrocarbon residue with 1 to 20 C atoms, $Sn(R^*)_3$ or $Si(R^*)_3$ in which R* each independently has the same meanings as R.

These borazines are reacted in the presence of a suitable combination of catalyst, base and acid trap (e.g. a zeolite) with silanes of the aforementioned formula (III) or with silanes of the type

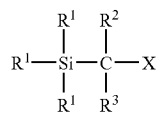

wherein each $R^1$ independently denotes hydrogen, halogen, a hydrocarbon residue with 1 to 20 C atoms, N(R')(R") or OR', in which R' and R" each independently represent hydrogen or a hydrocarbon residue with 1 to 20 C atoms, and $R^2$ and $R^3$ each independently denote hydrogen, halogen, N(R')(R") or OR' in which R' and R" each independently represent hydrogen or a hydrocarbon residue with 1 to 20 C atoms, X denotes hydrogen, halogen, $Sn(R^*)_3$ or $Si(R^*)_3$ in which each R* independently has the same meanings as R for the silylalkylborazines.

A borazine is particularly preferably used in this reaction in which the $R^4$ on the boron represents halogen and $R^4$ on the nitrogen represents hydrogen and a silane is used in which X=hydrogen.

The invention also concerns oligoborocarbosilazanes and polyborocarbosilazanes which can be obtained from the molecular silylalkylboranes or silylalkylborazines according to the invention, characterized in that each silicon atom has in a first coordination sphere at least one carbon atom which is bound to a boron atoms and this boron atom is additionally bound to two nitrogen atoms.

The oligoborocarbosilazanes or polyborocarbosilazanes in particular have the structural units Si—C—B—N—B—

C—Si, Si—C—B—N—Si—C—B or/and B—C—Si—N—Si—C—B. The said structural features are, for better clarity, linear sequences in which Si is of course always bound to four neighbouring atoms, B and N are always bound to three neighbouring atoms and C is in each case bound to three or four neighbouring atoms. The corresponding bonding dashes have been omitted to improve the clarity, but can easily be read by a person skilled in the art. Branches can occur at every atom.

The invention also concerns a process for producing such an oligoborocarbosilazane or polyborocarbosilazane in which a silylalkylborane of formula (I) or a silylalkylborazine of formula (X) is reacted at temperatures of −100° C. to 300° C. with a compound R'R"NH, in which R', R" each independently represents hydrogen or a hydrocarbon residue with 1 to 20 C atoms.

The molecular silylalkylborane or silylalkylborazine according to the invention is preferably reacted with at least the n-fold molar amount, in particular with at least the 2n-fold molar amount, where n denotes the number of sites in the molecule that can be cross-linked, and more preferably with an excess of ammonia and/or an organylamine of formula $H_2NR$ or $HNR_2$ in which R=H, $C_1$-$C_6$ alkyl, vinyl or phenyl per mole silylalkylborane with or without solvent at temperatures between −100° C. and 300° C.

The oligoborocarbosilazanes or polyborocarbosilazanes can also be formed from the precursor compounds, in particular the above-mentioned silylalkylboranes or silylalkylborazines, by direct polymerization of the single component precursor, in particular by polycondensation at temperatures between −100° C. and 500° C. It is not necessary to use ammonia or/and amines for the direct polymerization.

The invention also concerns a process which can be used to adjust the rheological properties of the oligoborocarbosilazanes or polyborocarbosilazanes which are produced in the form of liquid, viscous or solid polymers some of which are soluble and meltable by using ammonia or by temperature treatment. The degree of cross-linking of the oligoborocarbosilazanes or polyborocarbosilazanes can be adjusted by the type of polymer formation. The use of ammonia or amines results in highly cross-linked structures whereas mainly linear structures are obtained in the direct polymerization by temperature treatment e.g. at ≦500° C., preferably at ≦300° C. Hence oligoborocarbosilazanes or polyborocarbosilazanes having different desired rheological properties can be specifically prepared or the rheological properties of oligoborocarbosilazanes or polyborocarbosilazanes can be modified by an appropriate aftertreatment.

The oligoborocarbosilazanes or polyborocarbosilazanes are produced in the form of liquid, viscous or solid polymers some of which are soluble and meltable and can be subjected to various moulding processes, e.g. casting, spinning into fibres, pulling foils, preparing coatings by various coating processes such as dip coating or spin coating, before they are for example converted into silicon boron carbide nitride ceramics.

The invention additionally concerns a process for producing a silicon boron carbide nitride ceramic in which an oligoborocarbosilazane or polyborocarbosilazane according to the invention having the structural element Si—C—B (N)—N or a silylalkylborane of formula (I) or a silylalkylborazine of formula (X) is pyrolyzed in an inert or ammonia-containing atmosphere at temperatures between −200° C. and +2000° C. and subsequently calcined in an inert or ammonia-containing atmosphere at temperatures between 800° C. and 2000° C.

The inert atmosphere can be selected from a noble gas atmosphere for example an argon or helium atmosphere, a nitrogen atmosphere or an atmosphere of another inert gas which does not react with the reaction partners under the reaction conditions between 800° C. and 1700° C.

In a preferred embodiment of the process according to the invention the oligoborocarbosilazanes or polyborocarbosilazanes are heated for several hours at temperatures between 30 and 1000° C. They are subsequently preferably calcined in a nitrogen or argon atmosphere at temperatures between 1200 and 1600° C. and preferred heating rates of 1-100 K/min to remove hydrogen.

The invention also concerns silicon boron carbide nitride ceramics produced by the process described above from the oligoborocarbosilazanes or polyborocarbosilazanes according to the invention.

These ceramics preferably contain the N—Si—C—B—N structural element and in particular the structural unit Si—C—B—N—B—C—Si, Si—C—B—N—Si—C—B or/and B—C—Si—N—Si—C—B.

The ceramics according to the invention can be produced in the pyrolysis in a crystalline as well as in amorphous form. They are preferably in the form of a silicon boron carbide nitride powder. Due to their particularly advantageous properties, ceramics are preferred in which the elements N, Si, C and B are present in an amount of more than 93% by weight, in particular more than 97% by weight. The ceramic according to the invention has in particular a low oxygen content of <7% by weight, preferably <3% by weight and particularly preferably <1% by weight or <0.5% by weight.

The amorphous material can be crystallized to form a composite ceramic with at least one of the materials SiC, $Si_3N_4$, BN, C and $B_4C$ by age-hardening at a temperature of more than 1400° C. In such a composite ceramic the components are essentially homogeneously dispersed on a nanometre scale i.e. they are monodisperse. The composite ceramics according to the invention are especially characterized by their high temperature resistance and can be present completely or partially in a crystalline form in particular as a powder.

The oligoborocarbosilazanes or polyborocarbosilazanes, ceramics and composite ceramics can be used to produce ceramic powders, ceramic coatings, ceramic mouldings, ceramic foils, ceramic fibres or ceramic microstructures.

The silylalkylboranes, oligoborocarbosilazanes and polyborocarbosilazanes according to the invention can be used in a chemical vapour-phase deposition (CVD) or physical vapour-phase deposition (PVD). Ceramic coatings can be prepared by coating substrates by means of CVD or PVD. The vapour-phase deposition can be carried out as described in the prior art (see e.g. DE 196 358 48).

Microstructures can for example be produced by injection moulding or lithographic processes. The ceramics are suitable for manufacturing composite materials. The ceramics are particularly preferably produced in the form of fibres from which fabrics or meshes can for example be manufactured which can be used to increase the strength or toughness of other ceramics.

Another subject matter of the present invention is a process for producing a compound of formula (I)

$$(R)_3Si—C(R^1)(R^2)—B(R)_2 \quad \text{(I)}$$

in which R in each case independently represents a hydrocarbon with 1 to 20 C atoms, hydrogen, halogen, N(R')(R") or O(R') where R' and R" independently of one another denote hydrogen or a hydrocarbon with 1 to 20 C atoms and $R^1$ and $R^2$ independently denote hydrogen, halogen or a hydrocarbon with 1 to 20 C atoms. In the process according to the invention a silane of the general formula (VI)

$$(R)_3Si-C(R^1)(R^2)-X \quad (VI)$$

in which X denotes hydrogen, halogen or silyl residues is reacted with a borane of the general formula (VII)

$$B(R)_3 \quad (VII)$$

in the presence of a suitable combination of catalyst, base and acid trap in which R in each case independently represents a hydrocarbon with 1 to 20 C atoms, hydrogen, halogen, N(R')(R") or O(R') where R' and R" independently of one another represent hydrogen or a hydrocarbon with 1 to 20 C atoms.

Yet another subject matter of the present invention is a process for producing a compound of formula (I)

$$(R)_3Si-C(R^1)(R^2)-B(R_2) \quad (I)$$

in which R in each case independently represents a hydrocarbon with 1 to 20 C atoms, hydrogen, halogen, N(R')(R") or O(R') where R' and R" independently of one another denote hydrogen or a hydrocarbon with 1 to 20 C atoms and $R^1$ and $R^2$ independently denote hydrogen, halogen or a hydrocarbon with 1 to 20 C atoms, characterized in that a CH-acidic compound of the general formula (VIII)

$$(R)_3Si-C(R^1)(R^2)-H \quad (VIII)$$

is reacted in the presence of a suitable combination of catalyst, base and acid trap with a borane of the general formula (IX)

$$X-B(R)_2 \quad (IX)$$

in which R is defined as above and X represents halogen, NR'R" or OR' where R' and R" independently of one another denote hydrogen or a hydrocarbon with 1 to 20 C atoms.

An inorganic ion exchanger or a zeolite can be used in the two aforementioned processes as an acid trap.

The invention is elucidated in the following on the basis of some examples:

EXAMPLES OF APPLICATIONS

Example 1

Preparation of (trichlorosilyl)(dichloroboryl)methane

Reaction equations:

$$Cl_3Si-CH_2-Cl+Mg \rightarrow Cl_3Si-CH_2-MgCl \quad 1)$$

$$Cl_3Si-CH_2-MgCl+Cl-B(OC_2H_5)_2 \rightarrow Cl_3Si-CH_2-B(OC_2H_5)_2+MgCl_2 \quad 2)$$

$$Cl_3Si-CH_2-B(OC_2H_5)_2+2BCl_3 \rightarrow Cl_3Si-CH_2-BCl_2+2Cl_2B(OC_2H_5) \quad 3)$$

$$3Cl_2B(OC_2H_5) \rightarrow 3C_2H_5Cl+BCl_3+B_2O_3[\text{cat: AlCl}_3]$$

| | |
|---|---|
| chloromethyltrichlorosilane | 201 mmol, 36.9 g |
| magnesium | 288 mmol, 7.0 g |
| bis(ethoxy)chloroborane | 224 mmol, 23.3 g |
| boron trichloride | 488 mmol, 57.2 g |
| aluminium trichloride | 19 mmol, 0.5 g |

7.0 g magnesium powder is suspended in 150 ml absolute diethyl ether. The reaction is started by adding a few drops of chloromethyltrichlorosilane and optionally heating slightly. A solution of 36.9 g chloromethyltrichlorosilane in 200 ml diethyl ether is added dropwise to this suspension at 15° C. After the addition is completed, the reaction mixture is cooled to −78° C. and 23.3 g bis(ethoxy)chloroborane is added in one pour. The reaction mixture is heated to room temperature, the resulting magnesium chloride is removed by filtration and the filtrate is freed from solvent. 57.2 g boron trichloride is condensed on the residue at −78° C. The mixture is heated to room temperature to remove excess boron trichloride and the by-product ethoxy-dichloroborane is catalytically decomposed with 0.5 g aluminium trichloride. All volatile products are collected in a cold trap and fractionally distilled.

$^1$H-NMR (300 MHz, $C_6D_6$): δ=1.62-$^{11}$B-NMR (96 MHz, $C_6D_6$): δ=58.61-$^{13}$C-NMR (75 MHz, $C_6D_6$): δ=30.53(d)-$^{29}$Si-NMR (60 MHz, $C_6D_6$): δ=3.13.

Example 2

Preparation of (dichloromethylsilyl)(dichloroboryl)methane

Reaction equations:

$$Cl_2(CH_3)Si-CH_2-Cl+Mg \rightarrow Cl_2(CH_3)Si-CH_2-MgCl \quad 1)$$

$$Cl_2(CH_3)Si-CH_2-MgCl+Cl-B(OC_2H_5)_2 \rightarrow Cl_2(CH_3)Si-CH_2-B(OC_2H_5)_2+MgCl_2 \quad 2)$$

$$Cl_2(CH_3)Si-CH_2-B(OC_2H_5)_2+2BCl_3 \rightarrow Cl_2(CH_3)Si-CH_2-BCl_2+2Cl_2B(OC_2H_5) \quad 3)$$

$$3Cl_2B(OC_2H_5) \rightarrow 3C_2H_5Cl+BCl_3+B_2O_3[\text{cat: AlCl}_3]$$

| | |
|---|---|
| chloromethylmethyldichlorosilane | 197 mmol, 32.3 g |
| magnesium | 288 mmol, 7.0 g |
| bis(ethoxy)chloroborane | 224 mmol, 23.3 g |
| boron trichloride | 488 mmol, 57.2 g |
| aluminium trichloride | 19 mmol, 0.5 g |

7.0 g magnesium powder is suspended in 150 ml absolute diethyl ether. The reaction is started by adding a few drops of chloromethylmethyldichlorosilane and optionally heating slightly. A solution of 32.3 g chloromethylmethyldichlorosilane in 200 ml diethyl ether is added dropwise to this suspension at 15° C. After the addition is completed, the reaction mixture is cooled to −78° C. and 23.3 g bis(ethoxy) chloro-borane is added in one pour. The reaction mixture is heated to room temperature, the resulting magnesium chloride is removed by filtration and the filtrate is freed from solvent. 57.2 g boron trichloride is condensed on the residue at −78° C. The mixture is heated to room temperature to remove excess boron trichloride and the by-product ethoxy-dichloroborane is catalytically decomposed with 0.5 g aluminium trichloride. All volatile products are collected in a cold trap and fractionally distilled.

$^1$H-NMR (300 MHz, C$_6$D$_6$): δ=1.47 (CH$_2$); 0.47(CH$_3$)-$^{11}$B-NMR (96 MHz, C$_6$D$_6$): δ=58.61-$^{13}$C-NMR (75 MHz, C$_6$D$_6$); δ=29.28(d)-$^{29}$Si-NMR (60 MHz, C$_6$D$_6$): δ=23.85.

Example 3

Preparation of Tris(dimethylamino)silyl-bis(dimethylamino)boryl-methane

Reaction equation:

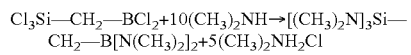

Cl$_3$Si—CH$_2$—BCl$_2$+10(CH$_3$)$_2$NH→[(CH$_3$)$_2$N]$_3$Si—CH$_2$—B[N(CH$_3$)$_2$]$_2$+5(CH$_3$)$_2$NH$_2$Cl

| | |
|---|---|
| (trichlorosilyl)(dichloroboryl)methane | 75 mmol, 17.3 g |
| dimethylamine | 3810 mmol, 171.8 g |

A solution of 17.3 g (trichlorosilyl)(dichloroboryl)methane in 200 ml absolute hexane is added dropwise to a solution of 171.8 g dimethylamine in 200 ml absolute hexane. After beating the reaction mixture to room temperature, the resulting dimethylamine hydrochloride is removed by filtration. The filtrate is freed from solvent and the residue is fractionally distilled.

$^1$H-NMR (300 MHz, C$_6$D$_6$): δ=2.45(SiNCH$_3$); 2.50 (BNCH$_3$).

Example 4

Reaction of (trichlorosilyl)(dichloroboryl)methane with monomethylamine

| | |
|---|---|
| (trichlorosilyl)(dichloroboryl)methane | 37 mmol, 8.5 g |
| dimethylamine | 1722 mmol, 53.5 g |

A solution of 8.5 g (trichlorosilyl)(dichloroboryl)methane in 120 ml absolute hexane is added dropwise to a solution of 53.5 g dimethylamine in 120 ml absolute hexane. After heating the reaction mixture to room temperature, the resulting monomethylamine hydrochloride is removed by filtration and the filtrate is freed from solvent. The polyborocarbosilazane remains as a clear viscous residue.

Example 5

Reaction of tris(dimethylamino)silylbis(dimethylamino)borylmethane with Ammonia

| | |
|---|---|
| (trichlorosilyl)(dichloroboryl)methane | 32 mmol, 8.7 g |
| ammonia | 5000 mmol, 85.0 g |

8.7 g tris(dimethylamino)silyl/bis(dimethylamino)boryl/methane is stirred into 85.0 g ammonia for 48 hours at −50° C. After removing the ammonia by distillation, the polyborocarbosilazane remains as a white solid residue.

Example 6

Preparation of B,B',B''-(trichlorosilylmethyl)borazine

Reaction equations:

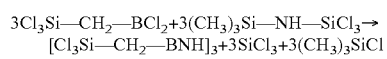

3Cl$_3$Si—CH$_2$—BCl$_2$+3(CH$_3$)$_3$Si—NH—SiCl$_3$→[Cl$_3$Si—CH$_2$—BNH]$_3$+3SiCl$_3$+3(CH$_3$)$_3$SiCl

| | |
|---|---|
| (trichlorosilyl)(dichloroboryl)methane | 36 mmol, 8.4 g |
| (trichlorosilyl)(trimethylsilyl)amine | 50 mmol, 11.2 g |

A solution of 8.4 g (trichlorosilyl)(dichloroboryl)methane in 20 ml hexane is added dropwise to a solution of 11.2 g (trichlorosilyl)(trimethylsilyl)amine in 50 ml hexane while stirring at room temperature. After a reaction period of 18 h, all volatile components are removed by distillation at 10 mbar and the residue is recrystallized from dichloromethane.

$^1$H-NMR (300 MHz, C$_6$D$_6$): δ=0.61 (CH$_2$); 4.50(NH)-$^{13}$C-NMR (75 MHz, C$_6$D$_6$): δ=16.98-$^{11}$B-NMR (96 MHz, C$_6$D$_6$): δ=32.74.

Example 7

Preparation of B,B',B''-(trichlorosilylmethyl)borazine

Reaction equations:

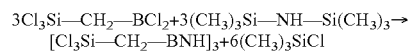

3Cl$_3$Si—CH$_2$—BCl$_2$+3(CH$_3$)$_3$Si—NH—Si(CH$_3$)$_3$→[Cl$_3$Si—CH$_2$—BNH]$_3$+6(CH$_3$)$_3$SiCl

| | |
|---|---|
| (trichlorosilyl)(dichloroboryl)methane | 43 mmol, 9.9 g |
| hexamethyldisilazane | 45 mmol, 7.3 g |

7.3 g hexamethyldisilazane is added dropwise to 9.9 g (trichlorosilyl) (dichloroboryl)methane while stirring at room temperature. After a reaction period of 12 h, all volatile components are removed by distillation in a high vacuum and the residue is recrystallized from dichloromethane.

Example 8

Preparation of B,B',B''-(methyldichlorosilylmethyl)borazine

Reaction equations:

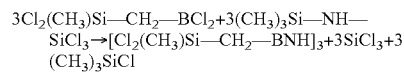

3Cl$_2$(CH$_3$)Si—CH$_2$—BCl$_2$+3(CH$_3$)$_3$Si—NH—SiCl$_3$→[Cl$_2$(CH$_3$)Si—CH$_2$—BNH]$_3$+3SiCl$_3$+3(CH$_3$)$_3$SiCl

| | |
|---|---|
| (methyldichlorosilyl)(dichloroboryl)methane | 62 mmol, 13.0 g |
| (trichlorosilyl)(trimethylsilyl)amine | 69 mmol, 15.4 g |

A solution of 13.0 g (methyldichlorosilyl)(dichloroboryl)methane in 30 ml hexane is added dropwise to a solution of 15.4 g (trichlorosilyl)(trimethylsilyl)amine in 70 ml hexane while stirring at room temperature. After a reaction period of 18 h, all volatile components are removed by distillation at 10 mbar and the residue is recrystallized from dichloromethane.

$^1$H-NMR (300 MHz, C$_6$D$_6$): δ=0.48(CH$_3$); 0.49(CH$_2$); 4.53(NH)-$^{13}$C-NMR (75 MHz, C$_6$D$_6$): δ=6.84(CH$_3$); 14.68 (CH$_2$)-$^{11}$B-NMR (96 MHz, C$_6$D$_6$): δ=33.60.

Example 9

Preparation of B,B',B''-(methyldichlorosilylmethyl)borazine

Reaction equations:

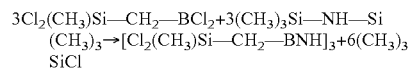

3Cl$_2$(CH$_3$)Si—CH$_2$—BCl$_2$+3(CH$_3$)$_3$Si—NH—Si(CH$_3$)$_3$→[Cl$_2$(CH$_3$)Si—CH$_2$—BNH]$_3$+6(CH$_3$)$_3$SiCl

| | |
|---|---|
| (methyldichlorosilyl)(dichloroboryl)methane | 55 mmol, 11.5 g |
| hexamethyldisilazane | 61 mmol, 9.8 g |

9.8 g hexamethyldisilazane is added dropwise to 11.5 g (methyldichlorosilyl) (dichloroboryl)methane while stirring at room temperature. After a reaction period of 12 h, all volatile components are removed by distillation in a high vacuum and the residue is recrystallized from dichloromethane.

Example 10

Reaction of B,B',B"-(trichlorosilylmethyl)borazine with monomethylamine

| | |
|---|---|
| B,B',B"-(trichlorosilylmethyl)borazine | 26 mmol, 12.0 g |
| dimethylamine | 1500 mmol, 46.6 g |

A solution of 8.5 g (trichlorosilyl)(dichloroboryl)methane in 120 ml absolute hexane is added dropwise to a solution of 53.5 g dimethylamine in 120 ml absolute hexane. After heating the reaction mixture to room temperature, the resulting monomethylamine hydrochloride is removed by filtration and the filtrate is freed from solvent. The polyborocarbosilazane remains as a clear viscous residue.

Example 11

Reaction of B,B',B"-(methyldichlorosilylmethyl) borazine with monomethylamine

| | |
|---|---|
| B,B',B"-(methyldichlorosilylmethyl)borazine | 22 mmol, 11.5 g |
| dimethylamine | 1500 mmol, 46.6 g |

A solution of 8.5 g (trichlorosilyl)(dichloroboryl)methane in 120 ml absolute hexane is added dropwise to a solution of 53.5 g dimethylamine in 120 ml absolute hexane. After heating the reaction mixture to room temperature, the resulting monomethylamine hydrochloride is removed by filtration and the filtrate, is freed from solvent. The polyborocarbosilazane remains as a clear viscous residue.

The invention claimed is:

1. Silylalkylborazine of formula (X):

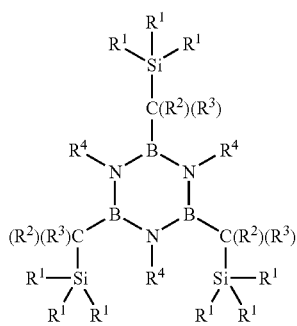

in which $R^1$ each independently denotes hydrogen, halogen, a hydrocarbon residue with 1 to 20 C atoms, $N(R')(R'')$ or $OR'$, in which $R'$ and $R''$ each independently represent hydrogen or a hydrocarbon residue with 1 to 20 C atoms and $R^2$ and $R^3$ each independently denote hydrogen, halogen, $N(R')(R'')$ or $OR'$ in which $R'$ and $R''$ each independently represent hydrogen or a hydrocarbon residue with 1 to 20 C atoms and $R^4$ each independently denote hydrogen, halogen, $N(R')(R'')$ or $OR'$ in which $R'$ and $R''$ each independently represent hydrogen, or a hydrocarbon residue with 1 to 10 C atoms or $Sn(R^*)_3$ or $Si(R^*)_3$ in which $R^*$ each independently denote $R^2$ or a hydrocarbon residue with 1 to 20 C atoms.

2. A process for the production of a silylalkylborazine as claimed in claim 1, comprising
reacting a silylalkylborane of formula (I)

with an amine $N(R^4)_3$ or an ammonium salt $HN(R^4)_3{}^+$ in which $R^4$ has the meaning stated in claim 1 and $A^-$ represents an anion.

3. A process for producing a silylalkylborazine as claimed in claim 1, comprising
reacting a borazine of formula (XI)

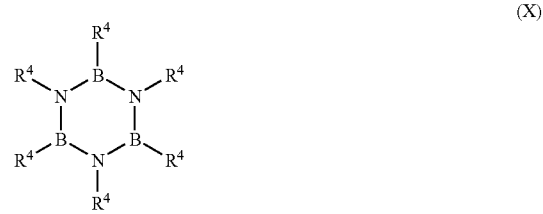

in which R4 in each case independently of one another denotes hydrogen, halogen, a hydrocarbon residue with 1 to 20 C atoms, $N(R')(R'')$ or $OR'$, in which $R'$ and $R''$ each independently represent hydrogen or a hydrocarbon residue with 1 to 20 C atoms, $Sn(R^*)_3$ or $Si(R^*)_3$ in which $R^*$ each independently has the same meaning as stated for R in claim 1, with silanes of the type

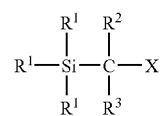

in which each $R^1$ independently of one another denotes hydrogen, halogen, a hydrocarbon residue with 1 to 20 C atoms, $N(R')(R'')$ or $OR'$, in which $R'$ and $R''$ each independently represent hydrogen or a hydrocarbon residue with 1 to 20 C atoms, and $R^2$ and $R^3$ each independently denote hydrogen, halogen, $N(R')(R'')$ or $OR'$ in which $R'$ and $R''$ each independently represent hydrogen or a hydrocarbon residue with 1 to 20 C atoms, X denotes hydrogen, halogen, $Sn(R^*)_3$ or $Si(R^*)_3$ in which $R^*$ each independently has the same meanings as R.

* * * * *